(12) United States Patent
Green

(10) Patent No.: US 6,605,306 B1
(45) Date of Patent: Aug. 12, 2003

(54) FOOD SUPPLEMENT FORMULATION

(76) Inventor: Lonny S. Green, 10825 Cherry Hill Dr., Glen Allen, VA (US) 23059

( * ) Notice: Subject to any disclaimer, the term of this patent is extended or adjusted under 35 U.S.C. 154(b) by 0 days.

(21) Appl. No.: 10/186,765

(22) Filed: Jul. 1, 2002

(51) Int. Cl.⁷ .................................................. A61K 35/78
(52) U.S. Cl. ...................... 424/733; 424/725; 424/94.65
(58) Field of Search ............................ 424/94.65, 733, 424/725

(56) References Cited

U.S. PATENT DOCUMENTS

| | | | |
|---|---|---|---|
| 4,444,751 A | * | 4/1984 | Cripps |
| 5,417,229 A | * | 5/1995 | Summers et al. |
| 5,707,630 A | * | 1/1998 | Morrow |
| 6,203,820 B1 | * | 3/2001 | Vickery |
| 6,431,874 B1 | * | 8/2002 | Szynalski |

FOREIGN PATENT DOCUMENTS

| | | | |
|---|---|---|---|
| GB | 2 096 996 A | * | 10/1982 |
| WO | WO 00/25795 A1 | * | 5/2000 |

OTHER PUBLICATIONS

Derwent abstract of PT 90393 A (1990).*

* cited by examiner

Primary Examiner—Francisco Prats
Assistant Examiner—Susan D. Coe
(74) Attorney, Agent, or Firm—Donald R. Fraser

(57) ABSTRACT

A food supplement formulation comprises quercetin, bromelain, papain, *passiflora incarnata, valeriana officinalis, gotu kola, usnea barbata, althea officinalis,* and L-arginine.

30 Claims, No Drawings

FOOD SUPPLEMENT FORMULATION

FIELD OF THE INVENTION

The present invention relates generally to a food supplement formulation. More particularly the invention is directed to a food supplement formulation which may additionally aid the relief of interstitial cystitis.

BACKGROUND OF THE INVENTION

Herbal formulations have been used as dietary supplements and natural medicaments for many years. In addition to providing compounds necessary to the human body for good nutrition, such formulations additionally may aid the body in dealing with a number of urinary tract maladies.

In addition to desiring a supplement to the daily diet, many persons suffer from a condition known as interstitial cystitis in which the afflicted person experiences frequent urination, pain in the genital/pelvic region, pain with sexual activity, and like maladies.

It would be desirable to prepare a beneficial herbal formulation that would act as a food supplement and might also simultaneously relieve the symptoms and manifestations of interstitial cystitis.

SUMMARY OF THE INVENTION

Accordant with the present invention, a beneficial herbal food supplement formulation has surprisingly been discovered. It comprises: quercetin; bromelain; papain; *passiflora incarnata; valeriana officinalis; gotu kola; usnea barbata; althea officinalis*; and L-arginine.

The food supplement formulation according to the present invention is useful to supplement the daily human diet, and additionally may be particularly useful for aiding the relief of interstitial cystitis.

DETAILED DESCRIPTION OF THE PREFERRED EMBODIMENT

The present invention is directed to a food supplement formulation comprising quercetin, bromelain, papain, *passiflora incarnata, valeriana officinalis, gotu kola, usnea barbata, althea officinalis*, and L-arginine.

Quercetin is a well-known natural compound useful as an anti-inflammatory agent and for generally promoting good cardiovascular health. Quercetin may be present in the inventive formulation at a concentration ranging from about 27 to about 55 weight percent. Preferably, the concentration of quercetin is about 45.6 weight percent.

Bromelain is a well-known natural compound which acts as an anti-inflammatory agent. Bromelain may be present in the inventive formulation at a concentration ranging from about 2 to about 5 weight percent. Preferably, the concentration of bromelain is about 3.7 weight percent.

Papain is a well-known natural compound useful as an anti-inflammatory agent and to aid digestion. Papain may be present in the inventive formulation at a concentration ranging from about 2 to about 5 weight percent. Preferably, the concentration of papain is about 3.7 weight percent.

*Passiflora incarnata* is a well-known herb which acts as an anti-anxiety and anti-spasmodic agent. *Passiflora incarnata* may be present in the inventive formulation at a concentration ranging from about 9 to about 40 weight percent. Preferably, the concentration of *passiflora incarnata* is about 27.4 weight percent.

*Valeriana officinalis* is a well-known herb useful as a smooth-muscle relaxant. *Valeriana officinalis* may be present in the inventive formulation at a concentration ranging from about 5 to about 15 weight percent. Preferably, the concentration of *valeriana officinalis* is about 9.1 weight percent.

*Gotu kola* is a well-known herb which acts as an anti-inflammatory agent and aid for tissue regeneration. *Gotu kola* may be present in the inventive formulation at a concentration ranging from about 1 to about 6 weight percent. Preferably, the concentration of *gotu kola* is about 2.4 weight percent.

*Usnea barbata* is a well-known material useful as an antibiotic and anti-inflammatory agent. *Usnea barbata* may be present in the inventive formulation at a concentration ranging from about 2 to about 8 weight percent. Preferably, the concentration of *usnea barbata* is about 4.6 weight percent.

*Althea officinalis* is a well-known herb which acts to sooth irritated and inflamed tissues. *Althea officinalis* may be present in the inventive formulation at a concentration ranging from about 0.5 to about 5 weight percent. Preferably, the concentration of *althea officinalis* is about 2.7 weight percent.

L-arginine is a well-known amino acid useful for aiding the body's immune system. L-arginine may be present in the inventive formulation at a concentration ranging from about 0.2 to about 8 weight percent. Preferably, the concentration of L-arginine is about 0.5 weight percent.

The aforementioned ingredients may be ground and mixed together by conventional mixing equipment. Thereafter, the powdered mixture may be pressed into tablets or placed in gelatin capsules for oral administration. The inventive food supplement formulation may additionally contain conventional fillers and extenders such as, for example, rice flower. Conveniently, the inventive food supplement formulation may be taken orally at a dosage rate ranging from about 300 to about 2,500 milligrams per day. Preferably, the dosage rate effective as a food supplement and possibly for relief of interstitial cystitis ranges from about 800 to about 1,500 milligrams per day.

EXAMPLE

The ingredients recited above are ground and mixed together in the quantities set forth in the following Table.

TABLE

Food Supplement Formulation

| Ingredient | Weight % |
| --- | --- |
| quercetin | 45.6 |
| bromelain | 3.7 |
| papain | 3.7 |
| passiflora incarnata | 27.4 |
| valeriana officinalis | 9.1 |
| gotu kola | 2.7 |
| usnea barbata | 4.6 |
| althea officinalis | 2.7 |
| L-arginine | 0.5 |
| Total | 100.0 |

The invention is more easily comprehended by reference to the specific embodiments recited hereinabove which are representative of the invention. It must be understood, however, that the specific embodiments are provided only for the purpose of illustration, and that the invention may be practiced otherwise than as specifically illustrated without departing from its spirit and scope.

What is claimed is:

1. A food supplement formulation, comprising:
   quercetin;
   bromelain;
   papain;
   *passiflora incarnata;*
   *valeriana officinalis;*
   *gotu kola;*
   *usnea barbata;*
   *althea officinalis;* and
   L-arginine.

2. The food supplement formulation according to claim 1, wherein the concentration of quercetin ranges from about 27 to about 55 weight percent.

3. The food supplement formulation according to claim 2, wherein the concentration of quercetin is about 45.6 weight percent.

4. The food supplement formulation according to claim 1, wherein the concentration of bromelain ranges from about 2 to about 5 weight percent.

5. The food supplement formulation according to claim 4, wherein the concentration of bromelain is about 3.7 weight percent.

6. The food supplement formulation according to claim 1, wherein the concentration of papain ranges from about 2 to about 5 weight percent.

7. The food supplement formulation according to claim 6, wherein the concentration of papain is about 3.7 weight percent.

8. The food supplement formulation according to claim 1, wherein the concentration of *passiflora incarnata* ranges from about 9 to about 40 weight percent.

9. The food supplement formulation according to claim 8, wherein the concentration of *passiflora incarnata* is about 27.4 weight percent.

10. The food supplement formulation according to claim 1, wherein the concentration of *valeriana officinalis* ranges from about 5 to about 15 weight percent.

11. The food supplement formulation according to claim 10, wherein the concentration of *valeriana officinalis* is about 9.1 weight percent.

12. The food supplement formulation according to claim 1, wherein the concentration of *gotu kola* ranges from about 1 to about 6 weight percent.

13. The food supplement formulation according to claim 12, wherein the concentration of *gotu kola* is about 2.7 weight percent.

14. The food supplement formulation according to claim 1, wherein the concentration of *usnea barbata* ranges from about 2 to about 8 weight percent.

15. The food supplement formulation according to claim 14, wherein the concentration of *usnea barbata* is about 4.6 weight percent.

16. The food supplement formulation according to claim 1, wherein the concentration of *althea officinalis* ranges from about 0.5 to about 5 weight percent.

17. The food supplement formulation according to claim 16, wherein the concentration of *althea officinalis* is about 2.7 weight percent.

18. The food supplement formulation according to claim 1, wherein the concentration of L-arginine ranges from about 0.2 to about 8 weight percent.

19. The food supplement formulation according to claim 18, wherein the concentration of L-arginine is about 0.5 weight percent.

20. A food supplement formulation, comprising:
   about 27 to about 55 weight percent quercetin;
   about 2 to about 5 weight percent bromelain
   about 2 to about 5 weight percent papain;
   about 9 to about 40 weight percent *passiflora incarnata;*
   about 5 to about 15 weight percent *valeriana officinalis;*
   about 1 to about 6 weight percent *gotu kola;*
   about 2 to about 8 weight percent *usnea barbata;*
   about 0.5 to about 5 weight percent *althea officinalis;* and
   about 0.2 to about 8 weight percent L-arginine.

21. The food supplement formulation according to claim 20, wherein the concentration of quercetin is about 45.6 weight percent.

22. The food supplement formulation according to claim 20, wherein the concentration of bromelain is about 3.7 weight percent.

23. The food supplement formulation according to claim 20, wherein the concentration of papain is about 3.7 weight percent.

24. The food supplement formulation according to claim 20, wherein the concentration of *passiflora incarnata* is about 27.4 weight percent.

25. The food supplement formulation according to claim 20, wherein the concentration of *valeriana officinalis* is about 9.1 weight percent.

26. The food supplement formulation according to claim 20, wherein the concentration of *gotu kola* is about 2.7 weight percent.

27. The food supplement formulation according to claim 20, wherein the concentration of *usnea barbata* is about 4.6 weight percent.

28. The food supplement formulation according to claim 20, wherein the concentration of *althea officinalis* is about 2.7 weight percent.

29. The food supplement formulation according to claim 20, wherein the concentration of L-arginine is about 0.5 weight percent.

30. A food supplement formulation, comprising:
   about 45.6 weight percent quercetin;
   about 3.7 weight percent bromelain
   about 3.7 weight percent papain;
   about 27.4 weight percent *passiflora incarnata;*
   about 9.1 weight percent *valeriana officinalis;*
   about 2.7 weight percent *gotu kola;*
   about 4.6 weight percent *usnea barbata;*
   about 2.7 weight percent *althea officinalis;* and
   about 0.5 weight percent L-arginine.

* * * * *